US00PP32371P2

(12) United States Plant Patent
Hansen

(10) Patent No.: US PP32,371 P2
(45) Date of Patent: Oct. 20, 2020

(54) ***AGAVE* PLANT NAMED 'JACK FROST'**

(50) Latin Name: *Agave ovatifolia*
Varietal Denomination: Jack Frost

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/873,126

(22) Filed: Feb. 5, 2020

(51) Int. Cl.
*A01H 5/12* (2018.01)

(52) U.S. Cl.
USPC ..... Plt./373

(58) Field of Classification Search
USPC ..... Plt./373
See application file for complete search history.

*Primary Examiner* — Annette H Para

(57) ABSTRACT

A new and unique *Agave* plant named 'Jack Frost' characterized by mounded plant habit of ovate, mostly flat, variegated leaves having wide creamy-white margins with bluish-green centers and minty-frosty-blue intermediate region. The leaves have large reddish-brown marginal and apical spines and frequently show imprints from marginal spines of leaves above or below. The plant is useful in the landscape as a specimen, en masse, or also in a container in the home or landscape.

2 Drawing Sheets

Botanical classification: *Agave ovatifolia.*
Variety denomination: 'Jack Frost'.

BACKGROUND OF THE INVENTION

The present invention relates to the new and distinct *Agave* plant, *Agave* 'Jack Frost' discovered by the inventor at a wholesale perennial nursery in Zeeland, Mich., USA as an uninduced whole-plant mutation from a tissue cultured crop of *Agave* 'Frosty Blue' (not patented) on Aug. 18, 2014. Prior to assigning the new plant a cultivar name, the new plant was identified through the evaluation process with the code 14-Sp-Agav-321B. The new plant has been successfully asexually propagated by division of offsets following removal of the meristem and also by shoot tip tissue culture at a nursery in Zeeland, Mich. Shoot tip tissue culture propagation systems have been found produce stable and identical plants that maintain the unique characteristics of the original plant.

No plants of *Agave* 'Jack Frost' have been sold, in this country or anywhere in the world, prior to the filing of this application, nor has any disclosure of the new plant been made prior to the filing of this application with the exception of that which was disclosed within one year of the filing of this application and was either derived directly or indirectly from the inventor.

BRIEF SUMMARY OF THE INVENTION

*Agave* 'Jack Frost' is a sport of 'Frosty Blue' which is a selection of *Agave ovatifolia*. 'Jack Frost' differs from its parent, 'Frosty Blue', as well as all other *Agaves* known to the applicant. The most similar known *Agave* cultivars other than the parent are: 'Flipper' (not patented), 'Killer' (not patented) and 'Orca' (not patented). 'Flipper' has a reverse pattern variegation to the new plant with the creamy white variegation on the inside of the leaves and the intense blue color on the margin. 'Killer' has foliage that is streaked with creamy-green and blue-green with a broad margin of creamy-green. 'Orca' has foliage with more muted margins of greyish-yellow.

*Agave* 'Jack Frost' differs from all other *Agaves* known to the applicant, by the combination of the following traits:

1. Foliage with medium, colorful, marginal spines protruding from broad variegated leaves;
2. Leaves have wide creamy-white margins and contrasting bluish-green leaf centers with a minty frosty blue in between the margin and the center;
3. Leaves are mostly flat ovate shaped;
4. Leaves show irregular imprint or indentation on adaxial and abaxial surfaces from leaves above or below;
5. Habit is mounded with mostly outright to horizontal foliage.
6. The marginal teeth and apical spine on mature leaves are reddish-brown.

BRIEF DESCRIPTION OF THE DRAWINGS

The photograph of the new plant demonstrates the overall appearance of the new plant including the unique traits as a five-year-old plant grown in a container in a greenhouse with supplemental water and fertilizer as needed. The colors are as accurate as reasonably possible with color reproductions. Ambient light spectrum, temperature, source and direction may cause the appearance of minor variation in color.

DETAILED BOTANICAL DESCRIPTION

Figure 1:
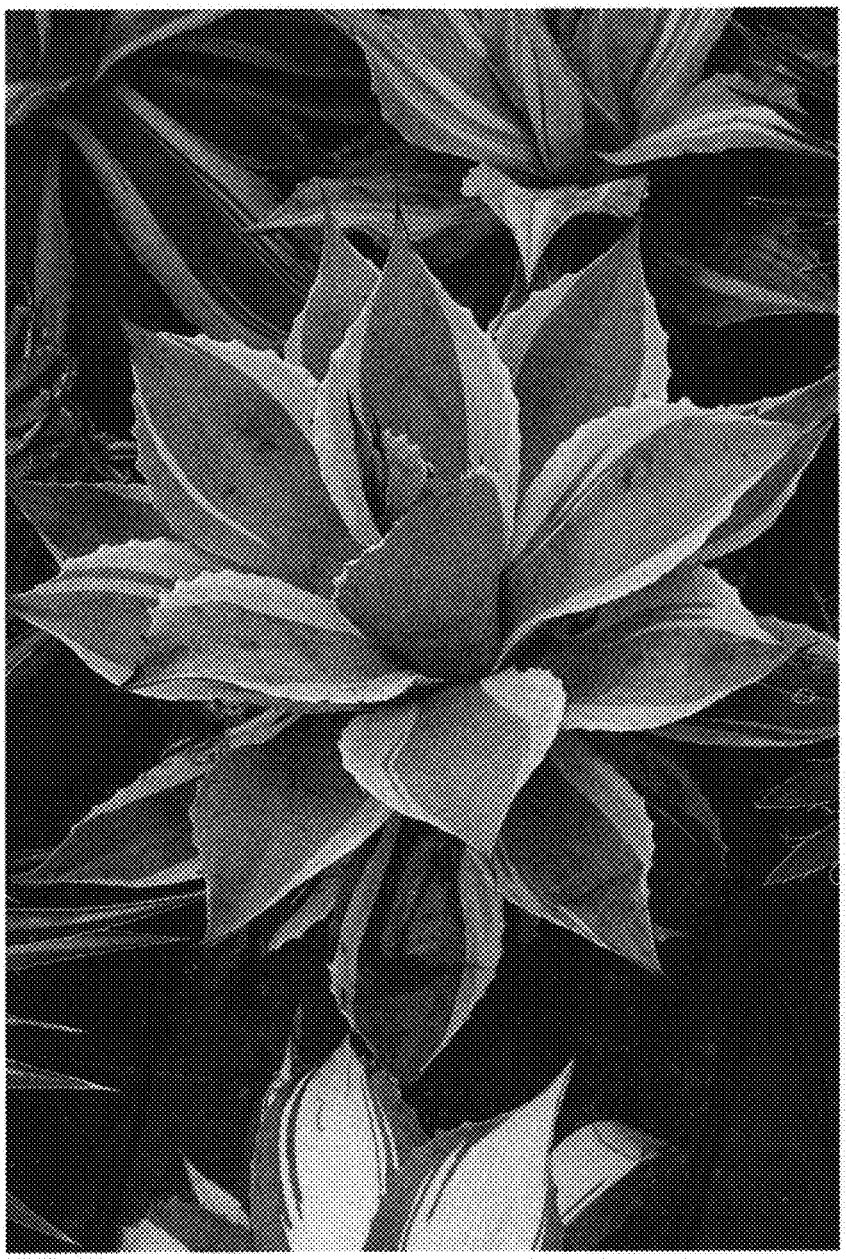
FIG. 1 shows the habit and variegation of the foliage of the whole plant.
Figure 2:
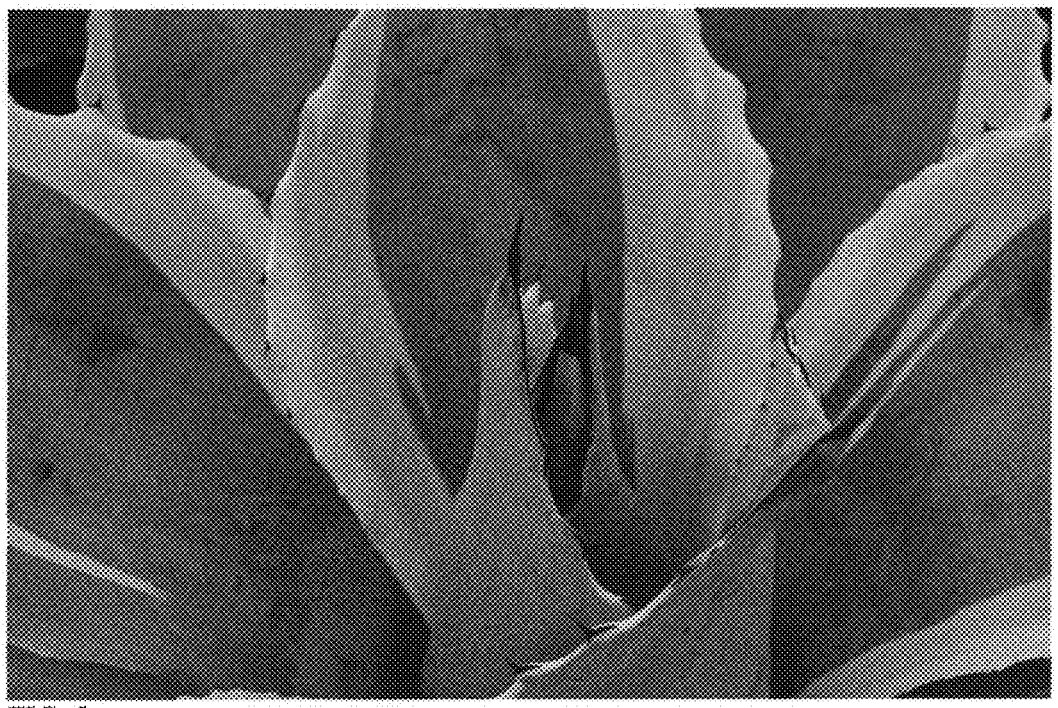
FIG. 2 shows a close-up of the new plant in a container with new unfurling foliage and marginal teeth and apical spines.

The following descriptions and color references are based on the 2015 edition of The Royal Horticultural Society Colour Chart except where common dictionary terms are used. The new plant, *Agave* 'Jack Frost', has not been observed under all possible environments. The phenotype may vary slightly with different environmental conditions, such as temperature, light, fertility, moisture and maturity levels, but without any change in the genotype. The following observations and size descriptions are of a five-year-old plant in a commercial wholesale greenhouse in Zeeland, Mich. with supplemental water and fertilizer as needed.

Botanical classification: *Agave ovatifolia;*

Variety denomination: 'Jack Frost';

Sport parentage: Uninduced whole-plant sport of *Agave* 'Frosty Blue';

Propagation: Division of offsets caused by removal of meristem and tissue culture;

Time to initiate roots: About 56 days;

Growth rate: Moderate to slow;

Crop time: About 20 weeks to finish during the summer in a 3.8 liter container from an established offset;

Rooting habit: Fleshy, lightly branching, with roots up to 20 cm long;

Root color: Nearest RHS 158C;

Plant shape and habit: Herbaceous tender perennial with basal rosettes of mostly flat, broad, variegated, whorled leaves emerging from broad central base, producing a symmetrical mound;

Plant size: Foliage height about 16.0 cm tall from soil line to the top of the leaves and about 26.5 cm wide at the widest point about just above soil line;

Foliage description: Ovate; simple; sarcous; acute apex ending in long stiff spine; truncate sessile base; distal margin with outwardly-pointing, sharp, stiff spines decreasing in stiffness and size in proximal portion; mostly flat; glabrous and heavily glaucous abaxial and adaxial; attitude outwardly to slightly upward;

Number of leaves: About 32 per plant;

Leaf size: To about 33.0 cm long, 17.5 cm wide near middle and 50 mm thick near base; average 30.5 cm long, 15.2 cm wide near middle and 44 mm thick near base;

Leaf variegation dimensions: Adaxial margin to 17.0 mm wide in longitudinal middle and tapering to about 2.0 mm near apex; abaxial margin to about 14.0 mm in longitudinal middle and tapering to about 1.0 mm at apex; adaxial intermediate zone between creamy-white margins and bluish-green center widest in longitudinal center and not noticeable at abaxial surface or adaxial base or apex, to about 38.0 mm wide in adaxial longitudinal center; adaxial bluish-green center about 6.5 cm wide; abaxial bluish-green center about 14.5 cm wide; with irregular narrow longitudinal stripes of bluish-green extending various random lengths into the intermediate zone and narrow creamy-white longitudinal stripes of various random lengths extending into the blue-green centers of both adaxial and abaxial;

Foliage fragrance: None observed;

Stem: To about 10.0 cm wide and about 8.0 cm tall; covered with leaves;

Leaf blade color:

*Mature adaxial*.—Outer margin nearest RHS NN155A, center nearest blend between RHS 122C and RHS 190B, intermediate zone nearest RHS N155A with undertone of RHS 122B.

*Mature abaxial*.—Margin nearest RHS NN155A, center nearest blend between RHS 122C and RHS 190B.

*Expanding young adaxial*.—Margin nearest RHS NN155, center nearest blend between RHS 122C and RHS 190B, intermediate zone nearest RHS N155A with undertone of RHS 122B.

*Expanding young abaxial*.—Margin between RHS NN155A to N155D, center blend between RHS 122C, RHS 190B and RHS N155A.

Apical spine: Stiff and sharp; to about 25.0 mm long, about 2.0 mm across at base; color nearest RHS 200B;

Marginal spines: Sharply pointed; stiff; distally pointing outwardly and slightly curved toward apex or base; lighter colored and decreasing in size, stiffness and separation in proximal portion; distally about 6.0 mm long and about 25.0 mm apart; proximally about 1.5 mm long and 5.0 mm apart; distal color nearest RHS 200B of mature leaves and nearest RHS 176B on younger leaves, color in proximal 5 cm of old and young leaves nearest RHS NN155B;

Petiole: Sessile;

Veins: Absent;

Flower description: Flowers have not yet been observed;

Fruit and seed: Have not yet been observed;

Disease resistance: *Agave* 'Jack Frost' has not been observed to be resistant to diseases common to *Agaves* beyond that which is normal for *Agave*. The plant is xeromorphic and survives well with minimal water once established. Hardiness at least from USDA zone 8b to 10. Full extent of winter hardiness has not been tested.

I claim:

1. A new and distinct cultivar of ornamental *Agave* plant named 'Jack Frost' as herein described and illustrated.

* * * * *